(12) United States Patent
Gault

(10) Patent No.: US 7,163,825 B2
(45) Date of Patent: Jan. 16, 2007

(54) BIO-REACTOR FOR TISSUE CULTIVATED IN FORM OF A THIN LAYER AND USES THEREOF

(75) Inventor: Philippe Gault, Orleans (FR)

(73) Assignee: Henkel KGaA, Dusseldorf (DE)

( * ) Notice: Subject to any disclaimer, the term of this patent is extended or adjusted under 35 U.S.C. 154(b) by 403 days.

(21) Appl. No.: 10/466,469

(22) PCT Filed: Mar. 8, 2002

(86) PCT No.: PCT/FR02/00834

§ 371 (c)(1),
(2), (4) Date: Jul. 15, 2003

(87) PCT Pub. No.: WO02/072750

PCT Pub. Date: Sep. 19, 2002

(65) Prior Publication Data

US 2004/0058434 A1 Mar. 25, 2004

(30) Foreign Application Priority Data

Mar. 9, 2001 (FR) .................................. 01 03242

(51) Int. Cl.
*C12N 5/00* (2006.01)
(52) U.S. Cl. .................................... 435/401; 435/289.1
(58) Field of Classification Search ................. 435/1.2, 435/366, 284.1, 289.1
See application file for complete search history.

(56) References Cited

U.S. PATENT DOCUMENTS

| 5,348,879 A | 9/1994 | Shapiro et al. |
| 5,882,929 A | 3/1999 | Bell et al. |
| 6,228,635 B1 * | 5/2001 | Armstrong et al. ...... 435/286.5 |

FOREIGN PATENT DOCUMENTS

WO   WO 97/26023   7/1997

* cited by examiner

*Primary Examiner*—James Ketter
(74) *Attorney, Agent, or Firm*—Nixon & Vanderhye P.C.

(57) ABSTRACT

The invention relates to a reactor for cell and tissue culture particularly suited to the culture of cells or tissues in the form of thin layers, and comprises the means for ensuring a physiological stimulation and supply of nutrients in culture medium adapted to the reduced thickness of the culture. The reactor can be used for the preparation of an implant and also includes the means of ensuring a mechanical stimulation of tissues or cells and supplying nutrients in culture medium suitable for structural tissues. The reactor also comprises, in an advantageous way, the means or a form that allows easy introduction of the tissue or the solid part of an implant into the culture chamber and, for example, a wall or an elastically deformable element. In addition, the reactor can include means of temperature regulation.

The reactor can be used for the culture of different types of cells and the preparation of implants in a variety of forms, compositions and applications.

43 Claims, 4 Drawing Sheets

BIO-REACTOR FOR TISSUE CULTIVATED IN FORM OF A THIN LAYER AND USES THEREOF

This application is the U.S. national phase of international application PCT/FR02/00834 filed 8 Mar. 2002 which designated the U.S.

The present invention relates to a cell and tissue culture reactor, optionally for the preparation of an implant, notably by cell growth and/or cellular differentiation, possibly in a biocompatible matrix and/or on an adhesion support.

The bioreactor is particularly suited to the culture of tissue or cells in a thin layer or layers, and comprises means of ensuring a physiological stimulation of the tissues or cells and providing nutrients in culture medium, suited to culture in a thin layer. The reactor also includes, in an advantageous manner, means or a form allowing easy introduction or extraction of tissue or the solid part of an implant in the culture chamber and, for example, a wall or an elastically deformable element. In addition, the reactor can includes means of temperature regulation.

The reactor can be used for the culture of different types of cells and the preparation of implants of a variety of forms, compositions and applications.

The present invention also relates to the process for the preparation of implants with the help of a bio-reactor according to the invention. Hence, the invention is useful notably for the preparation of dental, bone, cartilage implants, etc., comprising a tissue or a cell preparation, optionally, associated with a biocompatible matrix and/or a solid support or semi-solid adhesion support for cells or tissues or matrix.

A reactor for the manufacture of dental implants is known especially from document WO 00/21456. This reactor is able to accept an implant core including a radicular part and a coronary part. The core is made of an inert biocompatible material according to a form similar to that of an extracted tooth. The radicular part of the implant is immersed in a culture of mesenchymatous cells, in a culture medium the composition of which allows differentiation into cementoblasts and fibroblasts. This immersion is maintained for a sufficiently long time to allow adhesion of the cementoblasts to the radicular part, the formation of a first layer of cement and an outline of an alveolo-dental ligament attached to this cement.

The reactor is conceived to allow mechanical activation of tissue undergoing formation around the implant. This activation reproduces the physiological constraints to which a tooth is normally submitted. Indeed, physiological stimulation is needed to allow an in vitro proliferation and differentiation of the cementoblasts and fibroblasts.

In the reactor described in document WO 00/21456, the core of the implant is located in an alveola defined by a rigid porous wall through which culture medium diffuses. For activation of the cultured tissue, mechanical methods are located between the implant core and the reactor vessel. These means ensure a forwards and backwards displacement of the core of the implant with respect to the vessel. The displacement takes place notably along the length of the implant. The means of excitation include, for example, an electric activator.

Such a reactor is a delicate piece of equipment since it must allow precisely controlled guidance of the core of the implant with respect to the vessel. Indeed, the space between the wall of the alveola and the core should be maintained within a range of values determined for satisfactory growth of cementoblasts and fibroblasts. In addition, this reactor does not allow renewal or monitoring of the composition of the medium in which the cells are immersed. Also, the mechanical stimulation offered has certain limitations. Also, this reactor is described specifically for the preparation of a dental implant.

The aim of the invention is to provide reactors that are easier to manufacture and which allow satisfactory growth and/or differentiation of the cells in the reactor chamber, preferably within a matrix (e.g., extracellular matrix produced by cultivated cells or tissues) and at the surface of a support (for adhesion), more especially of cells or tissues cultivated in thin layers.

The specifications of this reactor are notably to allow the monitoring of several culture conditions to promote cell proliferation and differentiation, the production of extracellular matrix, and tissue organization and maturation. The bioreactor is more especially suited for the culture of tissues or cells in thin layers, notably structural tissue, for which there are many constraints and problems.

The first condition is a surface effect which allows a cellular adhesion or a tissue attachment to a biocompatible wall in the reactor or to two walls facing one another, separated by the culture space which then undergoes a double effect involving the surface or attachment.

The second condition is a mechanical effect generated within the tissue to get as near natural physiological conditions as possible. The constraints can involve pressure, stretching, shearing, rubbing or a combination of these effects.

Another constraint involves the supply of nutrients in culture medium, allowing good homogeneous growth of the tissue in a thin layer, i.e. homogeneous and controlled feeding of the medium in the reduced space of the culture.

These effects are important for in vivo and in vitro development, notably structural tissues, for example ligament, bone, cartilage, desmodonte, cement, aponevroses, ligament insertions involving bone, etc. These tissues are very sensitive to a physiological stimulation and there is a major benefit in cultivating them using these methods of activation.

Hence, the present invention provides for the first time a biological culture reactor, adapted for the culture of tissue in thin layers, ensuring a mechanical stimulation of the cells and the supply of nutrients and diffusion adapted to the nutritional medium. Advantageously, the reactor is also fitted with means for controlling the temperature and means allowing or facilitating the introduction or extraction of the solid part of an implant (like the adhesion support) in the culture space without altering the cells or tissues present.

Thus, an object of the invention more precisely relates to a reactor for the culture of cells or tissues in a thin layer or in thin layers. A particular characteristic of the reactor is it comprises (i) a culture chamber defining, between two walls, a culture space of between 1 and 1000 microns, preferably between 10 and 1000 microns, more preferably between 50 and 800 microns, (ii) mechanical means of stimulation of the cells or tissues in said space and (iii), preferentially, means of perfusion of the culture medium within the culture space.

The bioreactor according to the invention can allow biological tissues like these to be obtained for therapeutic or scientific or industrial purposes. This bio-reactor also allows the cultivation and development of tissues on the surface of an adhesion support or a prosthesis which will retain on their surface or on a part of their surface the cultivated tissue, for example to enhance or accelerate tissue scar formation and organic repair after the surgical insertion of the mixed implant or of said prosthesis so produced.

The invention can be employed with different types of implants, in a variety of forms, structures and compositions and for different applications. In the spirit of the invention, the term implant describes indeed any composition comprising cells or reconstituted tissue, which may be associated with a solid support. Preferably, it deals with an implant comprising a solid core (or a component) and a cellular or biological component. The core of the implant is also designated in the present document by the term <<adhesion support>> or heart of the implant. The core of the implant can be made of any biocompatible material, for example metal, plastic, polymer, glass, biological material, ceramic, bone, coral, etc. Typically, it consists of bioglass, ceramic (for example zircon), alloys, titanium or bone. The implant according to a specific example of the invention is a dental implant, comprising a core (radicular part) covered in part by cells by means of a reactor according to the invention. A dental implant, for example, can be prepared from any biocompatible material, for example metal (titanium for example), polymer, biological glass, ceramic, etc. It can also involve other types of implants, like for example a bone or joint implant.

As indicated above, the bioreactor according to the invention advantageously includes a culture chamber defining, between two walls, a culture space suitable for the production of tissue in a thin layer or in thin layers. Advantageously, it corresponds to a culture space of thickness less than or equal to about 1000 microns, generally of between about 10 and about 1000 microns, more preferably between 50 and 800 microns. Preferably, the culture space provides at least one zone of thickness less than or equal to 900 microns, more preferably about 800 microns, preferably between 50 and 800 microns. The reactor is suitable for the formation of biological tissues the thickness of which is controlled and thin, for example structural tissues, for example of the layer type.

The culture space is advantageously homogeneous within all or part of the culture chamber, in order to ensure the production of an essentially homogeneous cultivated tissue. Thus, the thickness of the culture space is advantageously constant in a key zone of the chamber.

The walls defining the culture space can be composed of or comprise different types of materials, which may or may not be rigid. Preferentially, the walls defining the culture space are of biocompatible material, for example polymer, glass, plastic, metal, etc. More preferentially, at least one of the walls is of a material that encourages cell proliferation, or cell adhesion, or reproduces a physiological situation. In this respect, especially preferred materials are bioglass, bone, coral, hydroxyapatite, titanium dioxide etc. (see also the examples). Thus, in a first method of achievement, the reactor comprises a culture space defined by two walls in biocompatible material, at least one of which is composed of or based on a material promoting cell culture, preferably in bioglass, bone, coral. The material promoting cell culture can be covered partly or completely by other biocompatible materials, like ceramics, metals or polymers.

According to the form of the bioreactor, the two walls can be fixed or mobile, as described later. Preferably, at least one of the two walls is mobile. In addition, one of the walls can be formed by the core of the implant itself. In this case, the reactor chamber is defined by a wall of a form suited to that of the core of the implant, introduction of which into the chamber creates the reduced culture space. In particular modes of realization, the reactor chamber is defined by a wall of conical or cylindrical form and the core of the implant is respectively conical or cylindrical. In this case, the reactor also has means of supporting the core of the implant, arranged or controlled such that the introduction of the core of the implant forms, with the wall of the culture chamber, a reduced culture space as defined above.

According to one particular variant of realization, the culture chamber of the reactor is delimited by a non rigid, elastically deformable wall, allowing easier introduction or removal of the core of the implant from the chamber, without altering the tissue. Hence, according to a preferred embodiment, the bioreactor also has means of introduction or removal of the core of an implant in the culture chamber. The invention also has as its aim to provide a reactor that allows improvement of the conditions of introduction or extraction of the adhesion support (or core) of an implant in the chamber or culture alveola, especially without damaging the tissues adhering to the surface of the core.

According to a particular method, the reactor is notably characterized by the presence of a membrane defining or bordering an alveola (or a chamber) for culture, cell differentiation and/or growth, said membrane being elastically deformable to help with the introduction of the cells or that of the adhesion support into said chamber. As will be described later in the text, the deformable membrane can also allow mechanical stimulation of the cells in said chamber.

To this end, the present invention proposes and has as its aim a reactor for the preparation of an implant, notably by cellular growth and/or differentiation, optionally within a biocompatible matrix, comprising an alveola for culture, cell differentiation and/or growth, characterized in that the alveola is defined by an elastically deformable membrane. Thus, the invention is based in part on the development of a chamber with a deformable wall, intended to receive the cells and, if necessary, the adhesion support (or core) of an implant. The use of such an alveola results in many advantages, and notably that of allowing easy introduction of the cells or of the adhesion support into said chamber.

Thus, for the preparation for example of an implant comprising cells associated with an adhesion support (solid part consisting for example of bone, polymer, biocompatible material, bioglass, teflon, metal, etc., also referred to as core of the implant), and optionally comprising an extracellular matrix, the reactor allows the carrying out of, under sterile and reproducible conditions, the culture, differentiation and/or growth of cells on the surface of the core of the implant. Indeed, by producing a deformation in the wall of the alveola, it is possible to introduce the core of the implant into this without any risk of significant rubbing between the core and the wall, and so without damaging the cells located on the surface of the core. In this method of manufacture, it is also possible to place the cells in gel or in a suspension or in an exogenous biological matrix or in an auto-secreted matrix, both in the vessel and on the core of the implant or prosthesis. In this case, the cells can be identical or very different in the vessel and on the core of the implant or the prosthesis.

In addition, the deformability properties of the wall, notably its elastic characteristics, allow, during the culture process, a mechanical stimulation of the cells, and encourage their proliferation and/or differentiation.

So, the present invention also has as its aim all bioreactors comprising a culture chamber defined by an elastically deformable wall. Thus, the vessel of the bio-reactor has, in an intermediate chamber, an elastic wall deformable by depression. In one preferred embodiment, the reactor according to the invention comprises means for the mechanical deformation of the wall, notably of a pneumatic or hydraulic nature.

As indicated above, the reactor according to the invention comprises advantageously means of mechanical stimulation of the cultivated cells or tissues. For that, the culture space can be submitted to constraints by relative movements of the two walls, the biological tissue or micromechanical attachment to one or two facing walls producing the mechanical stimulation.

The mechanical effect is preferentially exerted by pressure, by stretching, shearing, rubbing or by a combination of these effects. It is generally obtained by movement of one or both walls of the chamber, producing basically a change in the thickness of the culture space. Advantageously, the change in the thickness is produced by movement of one of the two walls, and is controlled such that it does not exceed + or − about 20% of the initial thickness of the culture space, preferably + or −10%.

It can be obtained by using deformable walls, flexible joints (notably toric joints) introduced into the structure of the culture chamber or between this and means of support of the walls, by mechanical stimulation (pressure, rotation, crushing, etc.) etc., as described below and in the examples.

In an especially preferred embodiment, the reactor comprises means of mechanical stimulation of the cells, for example by means of a piston, by displacement of the core of the implant, if necessary, or by deformation of the culture chamber or a part of it (for example by means of a deformable joint). In the case of a displacement, this can be for example carried out following the axis of the implant, by a forwards and backwards movement, or by a gentle partial rotation. In an advantageous manner, the stimulation is carried out by a deformable element (for example, supple), introduced into the reactor (alveolar membrane, joint, etc.) and by application of pressure/depression or a crushing force.

In addition, to increase the transmission of the constraints within the cultivated tissue, it is possible to add to the culture space elements such as absorbable or non absorbable sponges, for example a sponge made of collagen, chitosan or collagen-chitosan, or even irregularities of the surface of one of the walls, for example grooves, or even fibers of biocompatible polymer for example, or beads with a diameter of 50 to 1000 microns, preferably 50 to 500 microns, slightly less than the thickness of the culture space, and which can be made of polymer, glass, ceramic, etc., or else a combination of these materials.

One preferred embodiment of the invention relates to a bioreactor as defined earlier comprising (i) a culture chamber defining, between two walls, a culture space of thickness less than about 1000 microns, (ii) means of mechanical stimulation of the cells or tissues in said space and (iii), preferably, means of perfusion of the culture medium within the culture space, the culture space comprising also elements that allow the mechanical stimulation to be increased (sponge, fiber, bead, particle, etc.) or having at least one wall with irregularities (grooves, spray, fibers, etc.).

Another particular embodiment of the invention concerns a bioreactor as defined above, comprising (i) a culture chamber defining, between two walls, a culture space with a thickness less than about 1000 microns, (ii) means of mechanical stimulation of the cells or tissues in said space and (iii), preferably, means of perfusion of the culture medium within the culture space, at least one of the two walls being in a material promoting cell culture, preferably in bioglass or bone. The invention concerns, more generally, a bioreactor comprising a culture chamber, said chamber being defined by an internal wall made of or comprising bioglass or bone.

According to one preferred embodiment, the reactors of the invention also involve means of perfusion of the culture medium within the culture space. Another advantageous characteristic of the bio-reactors of the invention is to promote the diffusion of the nutritional medium in a culture space of reduced thickness, needed to obtain a surface and interface effect in the cultivated tissue. The diffusion of the medium is obtained by perfusion but its distribution is obtained by a periodic expansion-contraction of this space and/or a movement of amplitude as regular as possible on all the surfaces.

So, the effect resembles that of the pulse, and can be regulated in amplitude and frequency to give sufficient and suitable functional nutrition and stimulation without threatening to destroy the tissue. The frequency of stimulation (notably the expansion-contraction cycles is advantageously set at between 1 and 80 cycles per minute.

The angle between the movement axis of the rigid pieces constituting the culture interface and surface is a significant element for obtaining good regulation. For an elastic alveola, the variations in applied pressure in the intermediate chamber allow transmission of the effect of dilatation-contraction which then promotes the diffusion of the nutrient medium and functional stimulation, or a part of this stimulation, to the cultivated tissue. For example, the culture space can vary from 10% around a mean value of 50 to 1000 microns according to the cultures.

The number of entries and exits of the culture medium can be adapted to the tissue to be cultivated and the alveolar material. For an elastic alveola, an entry via the bottom of the vessel and an exit at the upper part is the simplest option. The entry can also take place from the implant core, for example. For a rigid alveola, in addition to or in place of the preceding solution, multiple entries and exits are possible in order to optimize the distribution of the medium in the culture space (FIGS. 5 and 6). Advantageously, the entries and exits are located at 90° to each other, the exits and entries alternating to obtain optimal diffusion of the medium. Hollow channels on the surface of the wall of the alveola can also help diffusion of the medium.

In a preferred embodiment, the reactor then also includes a perfusion system, allowing the supply of nutrients and/or renewal of the culture medium present in the alveola. The perfusion flow rate can be regulated by the man skilled in the art as a function of the type of cell and the type of culture, medium, etc. As indicated, the diffusion of the medium within the reduced culture space is advantageously promoted by the movement of one or both walls of the culture chamber (pressure, elastic deformation, forwards and backwards movement, etc.).

According to one particular embodiment, the reactors of the invention also include means for temperature regulation of the culture medium. Said means are for example circulating water or liquid or gas, at a controlled temperature, the presence of an electrical resistance, or a transistor, for example a Peltier-effect transistor.

In this respect, according to one particular embodiment, the invention also concerns any cell or tissue culture reactor, characterized in that it comprises a culture chamber and means of regulating the temperature of the culture chamber. Advantageously, it involves a reactor as defined above, with means of mechanical stimulation of the cells, and/or means of perfusion of the medium.

The reactors according to the invention can be used for the culture of different cell types and the preparation of implants of a variety of forms, compositions and applications. Preferably, it is used for the preparation of cell products comprising cells the growth, culture, differentiation and/or adhesion of which is promoted by a mechanical stimulation. Notably, one can cite fibroblasts, cementoblasts, chondrocytes, etc. Particular examples of cells are fibroblasts of the dermis, buccal mucosa, gums, alveolo-dental ligaments (desmodontal), chondrocytes, or precursors of these cells. In addition, the cell populations used can be mixed populations, comprising different cell types. The cells used in the invention can be autologous, allogenic or xenogenic. It can involve primary cultures or established lines. It involves, preferably, human cells or cells of human origin. They can be used in the form of a suspension, aggregates, colonies, layers, possibly in a natural or synthetic extracellular matrix allowing enhanced adhesion to the implant core. In addition, the cells can be genetically modified cells, i.e. containing a recombinant nucleic acid giving them beneficial properties.

The present invention also relates to the use of a bioreactor as defined earlier for the preparation of a tissue or cell culture or an implant. The present invention also relates to a preparation process for an implant, cultivated tissue or cell culture, using a reactor as defined above.

The composition or the cell tissue (which can comprise several types of cells) can be placed in the vessel of the bio-reactor before it is closed. Moreover, it can be placed in contact with the surface of the adhesion support of the implant or the prosthesis before placing these in the vessel of the bioreactor. These two techniques can be used simultaneously, by placing the cells in a gel or suspension or exogenous biological matrix or auto-secreted matrix, both, in the vessel and on the adhesion support of the implant or the prosthesis. In this case, the cells can be identical or different in the vessel and on the implant or prosthesis.

The bio-reactor is adapted to handle a culture space of relatively low thickness around the implant. Two situations can occur according to the form of the implant or prosthesis.

The piece can be placed in or taken out of the bio-reactor, without uprooting or scratching by rubbing the tissues adhering to its surface, due to a form called <<sloughing>> with respect to an axis of insertion and installation or withdrawn. The surfaces intended for culture can for example have a conical form.

If the core of the implant or prosthesis has a form liable to lead to rubbing of the cultivated surfaces, during installation in the bio-reactor or on withdrawal from the piece of the bio-reactor, it is advantageous to use a deformable alveola as described earlier, which can be distanced from the implant at such times.

In one particular embodiment, the invention has as its aim a reactor as defined above, for the preparation of an implant comprising a core covered with a matrix consisting in whole or in part of cells, said reactor including:

a membrane defining or bordering an alveola (or culture chamber) intended to receive all or part of the core of the implant;

means of support of said implant core in the alveola; and means of mechanical stimulation of cells around the implant;

characterized in that the membrane is elastically deformable and in that the means of mechanical stimulation include means of repeated deformation of said membrane.

A specific example of operation of the invention involves a reactor for the preparation of a dental implant by cell growth on a radicular part of the implant, comprising:

a membrane delimiting a reception alveola of the radicular part of the implant;

means of support of said implant with its radicular part in the alveola; and means of mechanical stimulation of cells on-the radicular part of the implant;

characterized in that the membrane is elastically deformable and the means of mechanical stimulation include means of deformation of said membrane.

In another particular embodiment, the invention has as its aim a reactor as defined above, for the preparation of an implant comprising a core covered by a matrix consisting in whole or in part of cells, said reactor including:

a flexible or rigid wall defining or bordering an alveola (or culture chamber) intended to receive all or part of the core of the implant;

means of support of said implant core in the alveola;

means of mechanical stimulation of cells around the implant; and means of perfusion of the culture medium in the alveola.

In one particular embodiment, the means of support of the core also include an elastically deformable element (for example a joint), ensuring movement of the implant in the alveola.

In another particular embodiment, the alveola is defined by a rigid wall consisting of or based on bioglass, bone or other biocompatible materials (polymer, glass, plastic, metal, or coral).

In another particular embodiment, the bioreactor also has means of temperature regulation.

In addition, the invention has as its aim a process for the manufacture of an implant by cell growth and/or culture and/or differentiation on a solid adhesion support (e.g., core of the implant) within a culture medium, said procedure including:

bringing into contact the core of the implant and cells, under conditions allowing the adhesion of cells to said core of the implant or to a part of it;

the immersion of at least a part of the core of the implant covered with cells obtained above in the alveola or the culture space of a bioreactor as defined above, previously or concomitantly filled with culture medium; and the mechanical activation/of the cells.

According to one particular embodiment, the process comprises:

bringing into contact the core of the implant and cells, under conditions allowing the adhesion of the cells to said core of the implant or to a part of it;

the immersion of at least a part of the core of the implant covered with cells obtained above in an alveola filled with culture medium, the alveola being defined or bordering an elastically deformable membrane; and the mechanical activation of the membrane for its deformation over time.

Another aim of the invention concerns a process for the manufacture of an implant by cell growth and/or culture and/or differentiation on a solid adhesion support (e.g., core of the implant) within the culture medium, said process including:

bringing into contact the core of the implant with cells, under conditions that allow the adhesion of cells to said core of the implant or to a part of it;

the immersion of at least a part of the core of the implant covered of cells obtained as above in an alveola filled with culture medium, the alveola being defined by an elastically deformable membrane and the alveola being previously deformed by radial expansion;

the cessation of deformation of the alveola; and the maintenance of the core of the implant in the alveola for a period long enough to allow cell growth and/or culture and/or differentiation on said core of the implant.

In the meaning of the invention, the term <<adhesion>> indicates the fact that the cells (possibly in a matrix) can be maintained in contact with the core of the implant, at least partially and temporarily, the time to introduce the core into the alveola or the reactor of the invention. This adhesion can be carried out by using surfaces that naturally ensure such adhesion or pretreated with this aim. It is also possible to incorporate the cells in a gel, paste, sponge, auto-secreted matrix, in order to facilitate this adhesion. It is also possible to cover the cells, after depositing them on the core of the implant, with a film that ensures their maintenance, preferably a porous film that is biodegradable.

As indicated above, a particular example of the application of the invention involves the preparation of a dental implant, by cell culture on the radicular part of said implant, introduced into a deformable alveola according to the invention.

The invention also has as its aim a process for cell culture, differentiation and/or proliferation, said procedure including:

the introduction of a cellular composition into an alveola filled with a culture medium, the alveola being defined by an elastically deformable membrane; and the mechanical activation of the membrane for its deformation over time.

As indicated earlier, in the process of the invention, the tissue is preferably perfused, in order to renew the culture medium. The perfusion is preferably ensured by the presence of an opening in the lower part of the alveola, ensuring the supply of fresh medium. This supply can also be achieved by a channel established in the core (or body) of the implant, or in a piston used for mechanical stimulation, should this be necessary. The removal of medium is generally ensured by an opening located in the upper part of the alveola.

The medium used for cell culture can be any medium known to a man skilled in the art, notably any medium suited to the culture, growth or differentiation of mammalian cells. In particular, it can be DMEM, RPMI, HAF medium, etc., possibly supplemented with antibiotics, amino acids, serum, etc.

The invention also concerns the use of a reactor like that described above, or an alveola like that described above, for the preparation of cell compositions, notably implants, typically for use in humans.

BRIEF DESCRIPTION OF THE DRAWINGS

Other aspects and advantages of the invention will appear on reading the examples that follow, which should be regarded as illustrative and not restricting, as well as illustrations in which.

Figure 1:
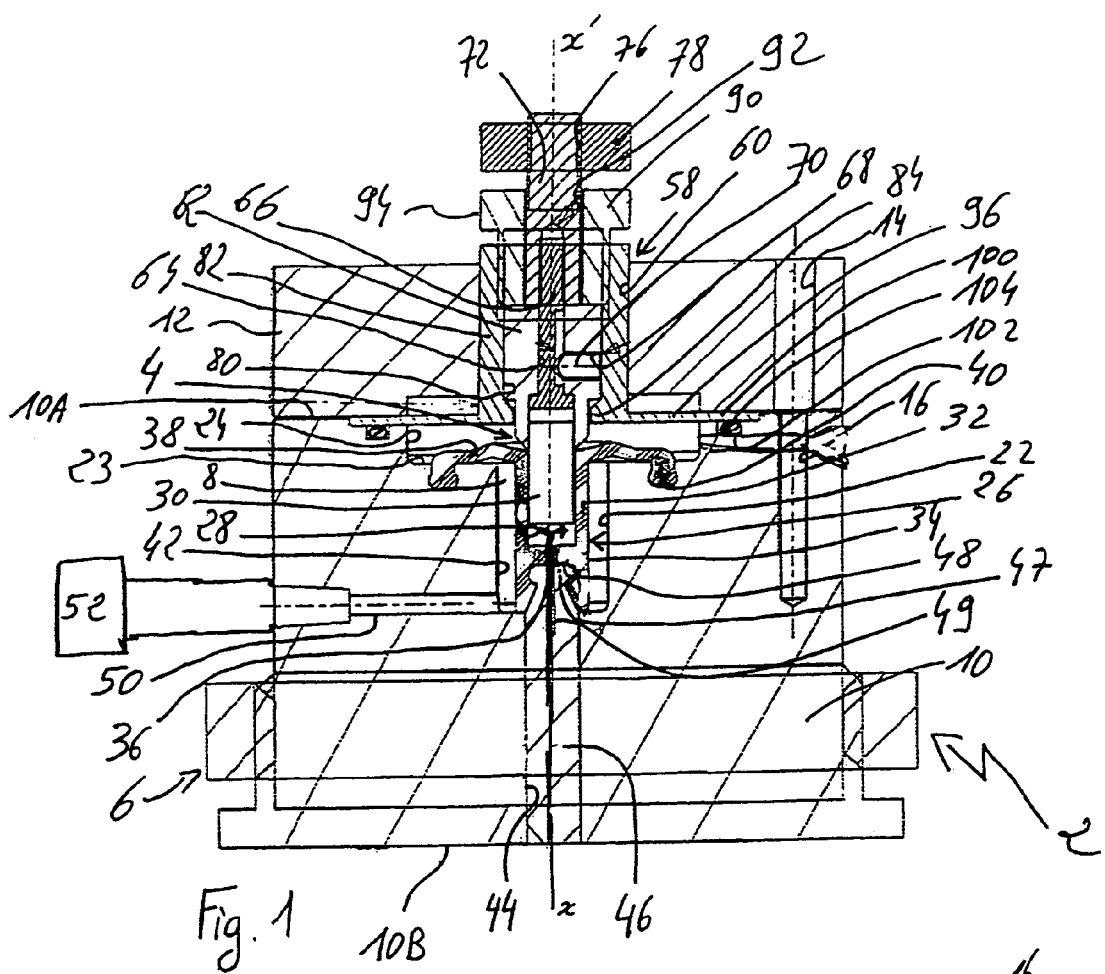
FIG. 1 is a longitudinal sectional view of a reactor according to the invention comprising a deformable wall.

Reactor 2 represented in FIG. 1 is notably intended for the manufacture of a dental implant by cell growth on a core of implant 4 made of a bio-compatible material. This core is formed for example of ceramic, titanium, bio-glass or a composite of these materials.

Reactor 2 generally rotates about the x–x'axis. It includes of vessel 6 defining an enclosure 8. Vessel 6 includes of a cylindrical body 10 and a cover 12 fused to the body. The body and the cover are both advantageously made of PTFE. It is understood that other materials can be used to make the reactor.

Figure 2:
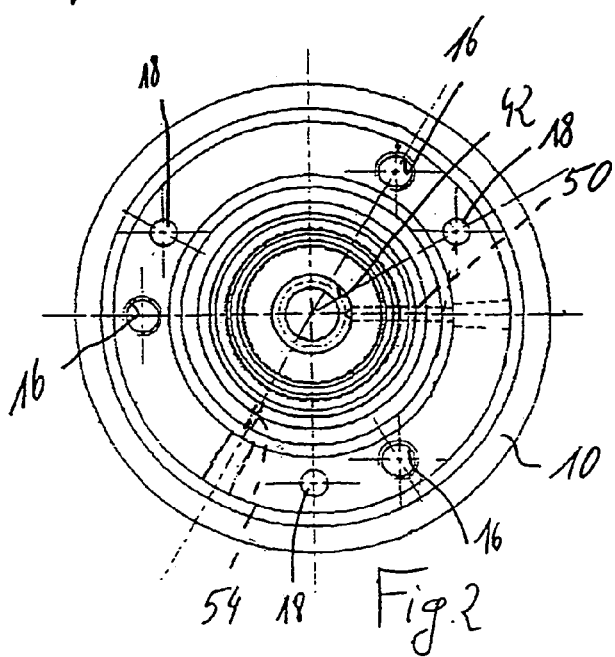
FIG. 2 is a top view of the reactor body according to the invention.

Cover 12 is fixed to the body 10 by three screws not shown. The screws are engaged in the passages 14 made through the cover 12. The drawn extremity of the screws goes into tapped holes 16 in the body 10. In addition, recessed holes 18, visible in FIG. 2, are made in the opposite faces of the cover and the body to receive centering pieces not shown.

The enclosure 8 includes an axial well 22 in the body 16. This well emerges at the center of the bottom generally plate 23 of a coaxial cuvette 24 hollowed out in body 10. This cuvette opens out on a first face of the flat extremity 10A of the cylindrical body 10.

An elastic membrane 26 in the form of a bell is located in the enclosure 8. This membrane defines a generally cylindrical reception alveola 28 of the radicular part, shown as 30, of the implant. The membrane 26 has a cylindrical section 32 sealed by a bottom 34 pierced axially by a channel 36. At the end opposite the bottom, the membrane has an exterior annulus 38 for interlocking membrane 26 to the body 10. This annulus is of the same material as the cylindrical section 32. It has on its face turned towards the bottom 34, a peripheral flange 40 in a peripheral cavity made in the bottom 23 of the cuvette.

The membrane 26 is impermeable to liquids and gases and is deformable. It is made for example from biocompatible silicone.

The interior diameter of the cylindrical section 32, i.e. the diameter of alveola 28 is very slightly greater than the diameter of the radicular part 30 of the implant. In particular, the difference in the diameters is such that when membrane 26 is at rest and is not deformed, the distance between the core of implant 4 in the alveola and membrane 26 is between 0.1 and 5 mm. The annular space formed between the core and the membrane corresponds to the region of tissue culture.

In addition, the exterior and interior diameters respectively of the cylindrical section 32 and of well 22 are such that an annular chamber 42 with a thickness that is not zero is formed between body 10 and membrane 26. The thickness of the annular chamber 42 is at least 1 mm. For example, it is 3 mm.

An axial bore 44 extends the well 22. This bore opens onto the second flat face of the extremity, shown as 10B, of the body. The axial bore 44 is normally sealed by a piece 46 clamped into this bore in order to seal it in a watertight manner.

One extremity of piece 46 projects to the interior of well 22. This extremity includes a protuberance 47 adapted to engage elastically with the interior of cavity 48 of a complementary form made in the thickness of bottom 34 of the membrane. In addition, piece 46, includes an internal channel 49 coming out axially at the summit of the protuberance 47 with respect to passage 36 in the bottom 34 of the membrane. Channel 49 leads, at the other extremity, to piece 46, at the exterior of the reactor. Thus, channel 49 supplies culture medium to the alveola, by means of any suitable device (pump, syringe, etc.). Channel 49 can also have a bend, allowing it to come out on the lateral wall of the reactor.

A channel 50 connected to annular chamber 42 is achieved by the body 10. This channel is adapted to link chamber 42 to a source of variable depression, indicated by 52. This source of variable depression is for example represented by a vacuum pump.

Channel 50 extends radially and opens on to the lateral wall of the cylindrical body 10 where it acts as a connection to the source of depression 52.

Figure 3:
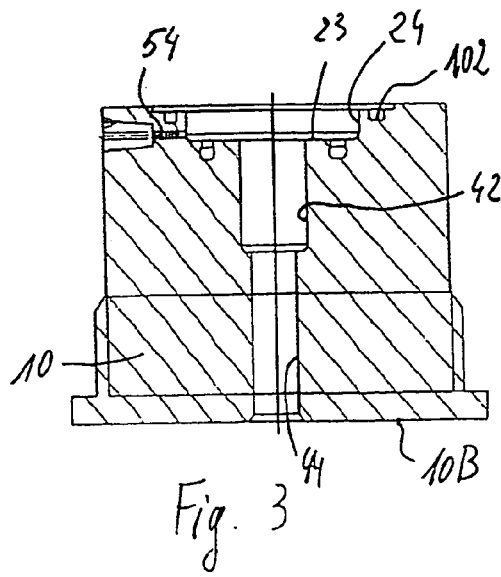
FIG. 3 is a longitudinal sectional view of the body of the reactor according to the invention.

In addition, an evacuation channel 54, seen on FIGS. 2 and 3, runs through body 10 for the circulation of culture medium in which the radicular part 30 of the implant is immersed. This channel opens, at the first extremity, into cuvette 24 and, at the other extremity, through the cylindrical wall of body 10. This channel is made so that it can be linked to a collector 56 of culture medium.

In addition, reactor 2 includes means 58 to support core 4 of the implant in a fixed position relative to vessel 6 and enclosure 8.

These means of support are achieved through a central orifice 60 crossing the cover 12.

The means of support 58 include a support piece 62 represented on its own in FIG. 3. This piece 62 is generally able to rotate. It includes an axial shouldered passage 64 which receives a rod, indicated by 66, which axially extends the core 4 of the implant.

A hole tapped through 68 is made radially through the wall of piece 62. This hole receives a headless screw 70 to hold the implant with respect to the piece. The extremity of screw 70 abuts a flat part of rod 66, thereby ensuring it axial immobilization and rotation.

Shaft 66 extends beyond piece 62 to its other extremity at the core of implant 4. This extremity of the shaft is linked to axial bolt 72. This bolt includes, axially at one extremity, a seating which receives the extremity of shaft 66. This latter is held in place by adhesive. At its other extremity, bolt 72 includes an exterior thread 76 which carries a nut 78.

Piece 62 passes into a chamber 80 defined by a cylindrical ferrule 82. The ferrule defines a cylindrical passage leading on to its two extremities and the length of which defines chamber 80.

At one extremity, the diameter of the passage is reduced by a sunken peripheral rim 84 forming a diaphragm. This sunken rim defines an annular surface to support piece 62.

At the other extremity of the passage, ferrule 82 presents a tapping adapted to receive a threaded filling plug 90 keeping piece 62 in contact with rim 84. Plug 90 is crossed axially by bore 92 for the passage of bolt 72. It carries a suitable exterior thread to match the tapping. Beyond the thread, plug 90 has a serrated crown 94.

Ferrule 82 has at its extremity with rim 84 an exterior annulus 96 adapted so that it can be inserted between body 10 and cap 12. This annulus has a diameter greater than the diameter of cuvette 24. Its exterior peripheral rim is received partially into annular impression 100 made in the first principal face 10A of the body around cuvette 24. This impression 100 has a flat bottom in which is located an annular canal 102 which takes a watertight toric joint 104.

The depth of impression 100 is less than the thickness of annulus 96 in order that annulus 96 and ferrule 82 remain held tightly between the bottom of impression 100 and cover 12.

For the manufacture of an implant, for example a dental one, the reactor is first assembled as shown in FIG. 1 while the core of the implant is not in place at that time.

In particular, membrane 26 is inserted into well 22, and ferrule 82 is engaged in orifice 60 of the cover. The cover being immobilized on body 10, ferrule 82 is held in place by annulus 96 inserted between the body and the cover.

In addition, core 4 of the implant is fixed to the piece of support 62 by screw 70 retaining rod 66 extending the core.

After fixing the core to the support piece, the radicular part of the core is incubated in the presence of a cell mixture under conditions that ensure the adhesion of the cells to said radicular part. For the preparation of a dental implant, the cell composition typically comprises fibroblasts of the alveolo-dental ligament and/or precursors of these fibroblasts and cementoblasts. In one particular embodiment, the radicular part of the core is covered with a cell tissue. This cell tissue has undergone earlier plate culture then wound around the radicular part of the core of the implant. In another embodiment, the radicular part of the core is covered in a matrix impregnated with cells, for example of the sponge, gel, paste type, etc.

In order to allow the insertion of core 4 covered in this way into the reactor, without risking damage to the cell tissue, a depression is made in annular chamber 42. This depression is created by pump 52. Under the action of this depression, membrane 26 is deformed notably by radial expansion of its cylindrical section 32.

Alveola 28 finds itself thus dilated increasing its interior section. The core of the implant is then introduced into reactor 2 via the cover passage. The radicular part of the core is inserted into alveola 28. To keep the core of the implant in place, plug 90 is engaged around bolt 72 and is screwed into sleeve 82. The screwing is continued until support piece 62 is closed and immobilized axially between lip 84 and plug 90.

After the initial insertion of the core of the implant, alveola 28 is relaxed by stopping the depression created in chamber 42. It is understood that the invention is not limited to this mode of use, and that it is possible to bring into direct contact the implant and the cell material in the alveola of the reactor.

For the culture of cell tissue, alveola 28 is permanently perfused with culture medium introduced via bottom 34 of the membrane by channel 49. So, the culture, medium circulates in alveola 28 along core 4 and exits via the upper part of the alveola emptying into cuvette 24. The culture liquid is removed from cuvette 24 by evacuation channel 54.

During the cell culture or growth phase, membrane 26 undergoes repeated cycles of elastic deformation. Each cycle includes a first phase which increases the volume of alveola 28 by establishing a depression in the watertight chamber 42 and a second phase during which watertight chamber 42 is opened to the air to stop the depression leading to a reduction in this volume during relaxation of the membrane by elasticity.

This cyclic depression is produced by the source of depression 52 connected to chamber 42 by channel 50.

The deformation of the membrane produces a mechanical action on the cells undergoing culture. In addition, the pulsations created by the membrane in the culture medium encourages the diffusion of this in alveola 28.

The depression created by the source is periodic and its frequency can approach that of the natural pulse, although this need not be considered necessary for the result. For a human being, this frequency is such that 40 to 80 beats take place every minute. In the bioreactor, a pulsation every three to ten seconds can be sufficient. The periodic depressions created in chamber 42 are advantageously repeated throughout the entire period of cell culture. They produce a physiological stimulation of the cells, necessary to promote tissue development.

As a variation and in order to increase further the effect of diffusion of the culture medium under the action of deformation of the membrane, chamber 42 defined between membrane 26 and body 10 is divided into compartments by separating walls. Each closed compartment so created is linked to its own source of depression. The sources of depression are activated successively to ensure successive deformations of the membrane and so create a wave that is propagated along membrane 26. This wave produces a pulsatile phenomenon in the culture space formed between the membrane and the core of the implant.

In yet another variant, the culture medium is perfused at several points distributed horizontally along the circumference of the vessel. The points of entry and exit of the culture medium are situated here and there on the core of the implant in multiple points on a vertical plane but diametrically opposed to the core of the implant.

The entry and exit points are advantageously distributed following vertical lines, but at 90° to one another in the plane and alternate to obtain an optimal diffusion of the medium. The entry and exit points can be switched periodically so that all the cells are irrigated in a similar manner.

As described earlier, the angle between the axis of movement of the rigid pieces forming the culture interface and surface is an important item as far as good control is concerned. For an elastic alveola, the variations in the applied pressure in the intermediate chamber allow transfer of the effect of dilatation-contraction which promotes diffusion of the nutrient medium and functional stimulation, or a part of this stimulation, to the cultivated tissue. For example, the culture space can vary by 10% around a mean value of 50 to 1000 microns according to the cultures.

The number of entries and exits for the culture medium can also be adapted to the tissue to be cultivated and the alveolar material. For an elastic alveola, an entry via the bottom of the vessel and an exit via the upper part is the simplest option. For a rigid alveola, in addition to the preceding solution, multiple entries and exits are possible to optimize the distribution of the medium in the culture space. Hollow surface channels in the wall of the alveola can also help diffusion of the medium.

At the outlet of the cell culture, core 4 covered with cultivated cells is removed from the reactor through cover 12. During the extraction, alveola 28 remains dilated by a depression created in chamber 42.

Figure 4:
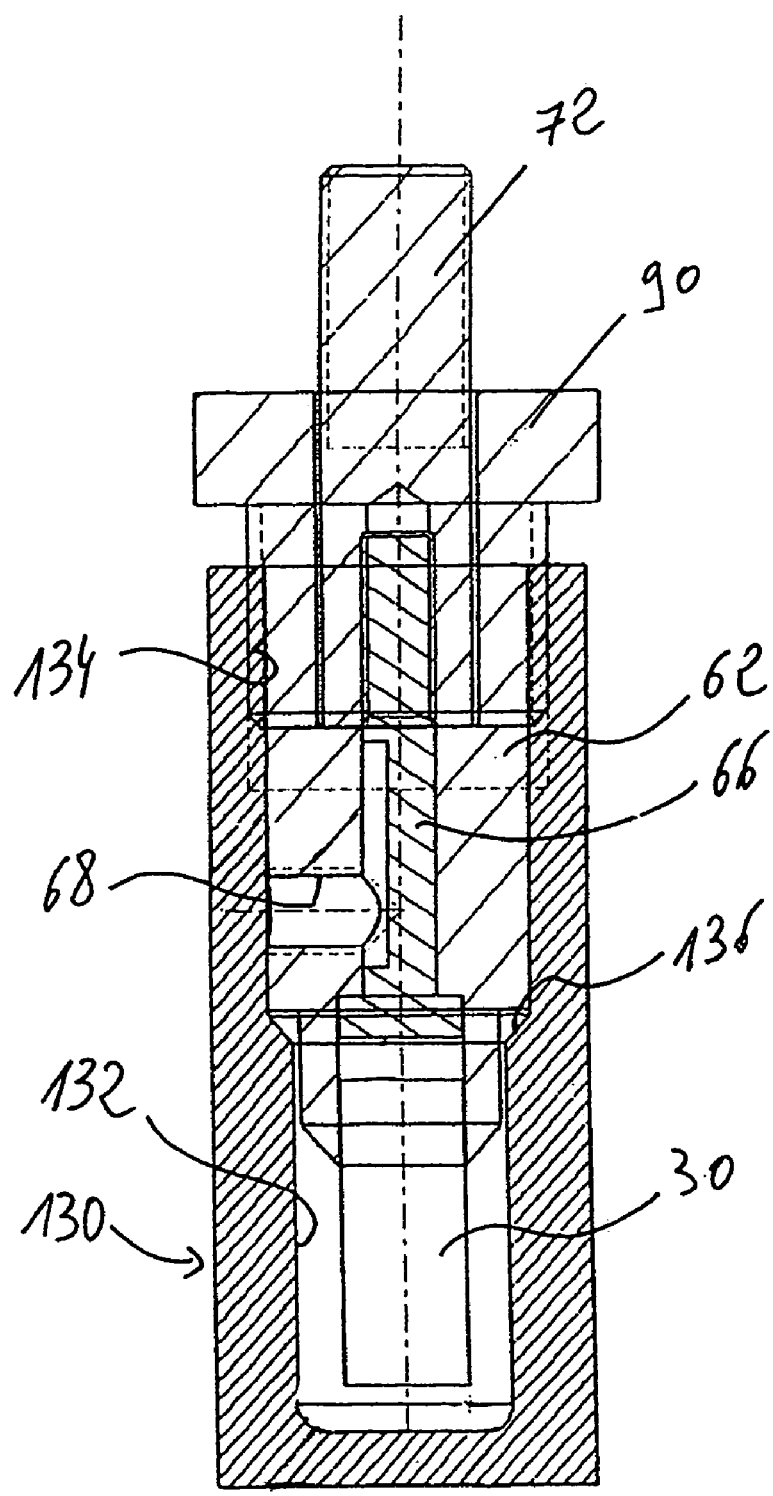
FIG. 4 is a longitudinal sectional view of a transport container of a dental implant.

For storage and transport to the place where the surgical procedure is to take place, the implant is kept in cylindrical container 130 illustrated in FIG. 4. This container has a cylindrical cavity 132 suitable for receiving the radicular part of the implant covered in cells.

At its open extremity, cylindrical cavity 132 has a tapping 134 which allows screwing of drawn plug 90.

Between the bottom of the cavity and tapping 134, the cavity has a shoulder 136 forming a support surface for support piece 62.

After screwing plug 90, the support piece is axially immobilized by being held tightly between shoulder 136 and plug 90.

The distance between the bottom of the cavity and shoulder 136 is such that when support piece 62 is in contact with shoulder 136, the radicular part of the implant is not in contact with the wall of the cavity at any point.

For storage of the implant, the cavity is filled with preservation liquid in which the radicular part of the implant is immersed.

Figure 5:
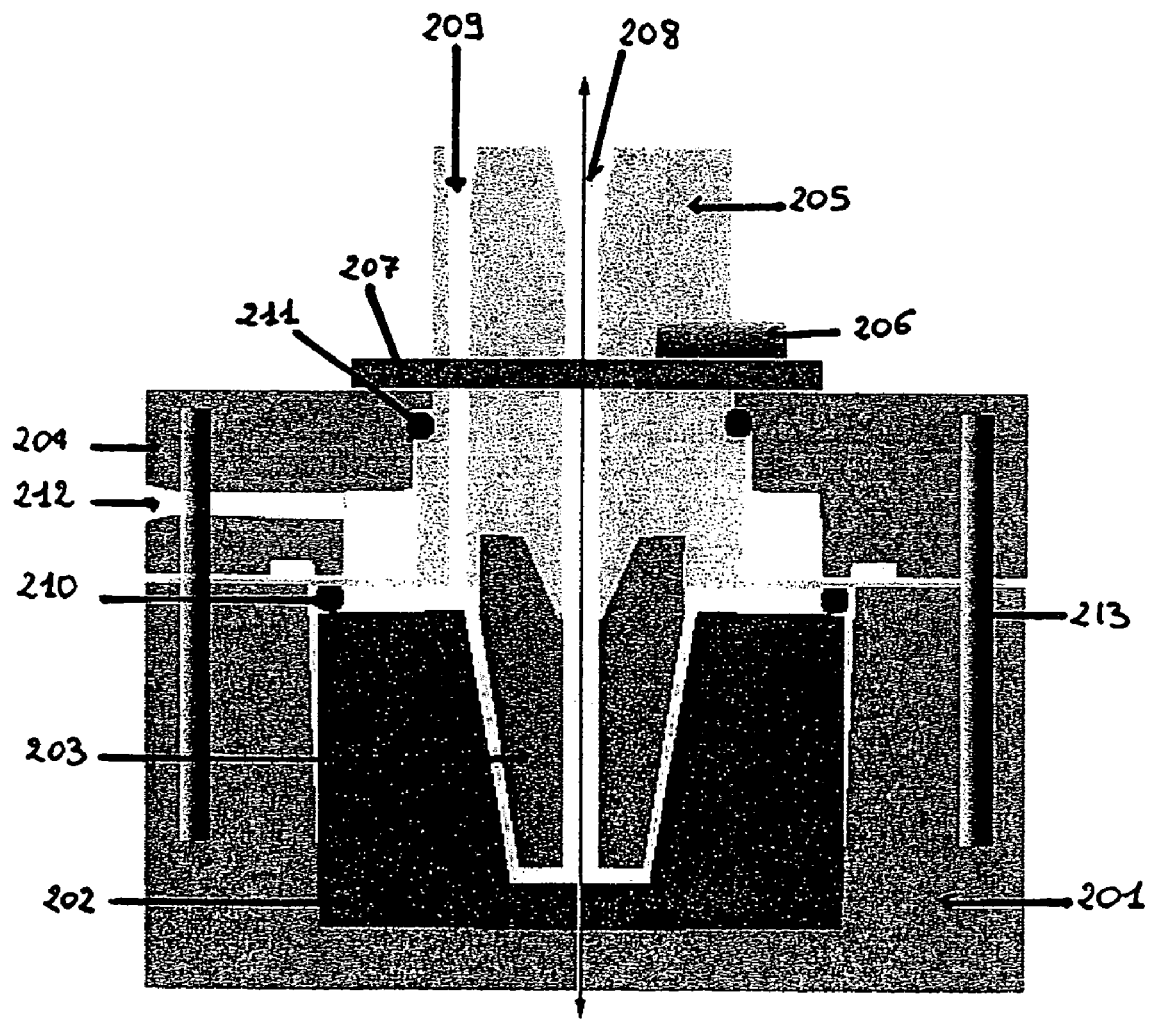
FIG. 5 is a view of a longitudinal section of a reactor according to the invention, perfused for the culture of chondroblasts, including a rigid wall, with functional stimulation.

The reactor shown in FIG. 5 comprises a vessel 202 which is made for preference of bio-glass with a trunk-cone concavity to ensure the interface with internal cone 203 and so allow a mechanical stimulation of the gel culture with a pressure effect and shearing-rubbing which approximates the physiological conditions that cartilages are subject to. The size of the device can be adapted to the culture surface desired (trunk-cone), and hence the quantity of cells. The trunk of internal cone 203 can also be, for preference, of bio-glass or any other material which mimics as far as possible the bone support. The flatter the cone is, the greater will be the variations in pressure and the diffusion of the medium, and the constraints in reduced shearing, and vice versa.

Vessel 202 can be inserted into vessel 201 fitted with a cover 204 and having a flat bottom to allow possible use of the reactor on a heating table and thereby ensure a homogenous temperature distribution. The temperature control system can also be directly incorporated in the wall of vessel 201 of the bio-reactor. It can, for example, involve a circuit of water or even an electrical resistance or a Peltier-effect transistor, etc. Two centering axes 213 are inserted in cover 204 and body 201.

In cover 204 there is also an entry 212 intended to allow the passage of compressed air responsible for movement and which thereby allows mechanical stimulation. A lower toric joint 210 governs the amplitude of the vertical movement applied to the medium. It is also possible to add to the device an upper toric joint 211 which promotes the amplitude of the vertical movement applied by pressurized air.

The device also comprises a mobile cylindrical part 205 fitted with a lower diaphragm and carrying the internal cone. In this mobile part, an entry 208 allows perfusion of the culture medium and an exit 209 ensures its removal. A washer 207 associated with a spring lamina or a return silicone washer, allows, by its thickness, regulation of the height of the movement imparted by mobile part 205. A blocking rod or stirrup 206 restricts the vertical movement by coming into contact with washer 207.

Figure 6:
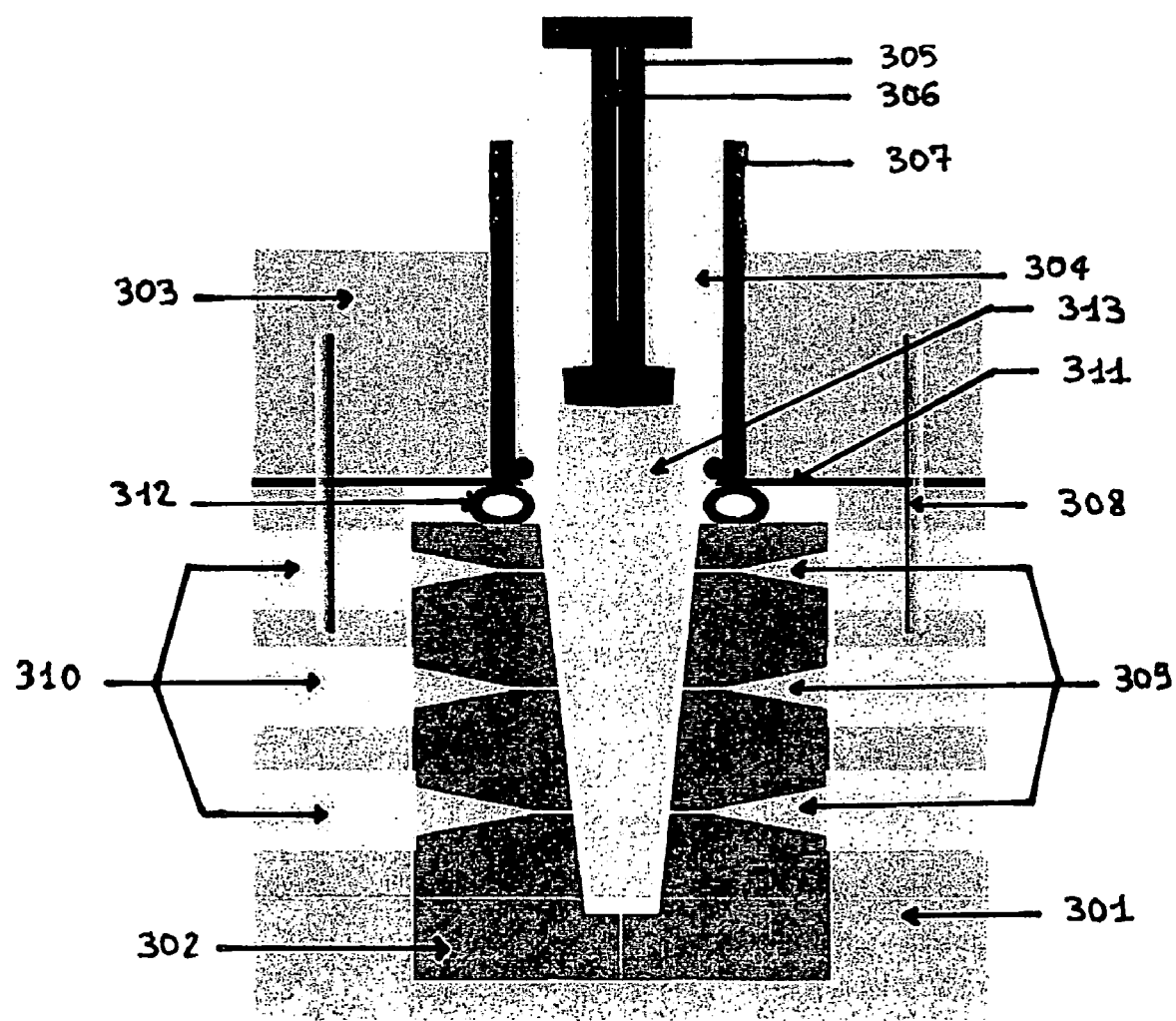
FIG. 6 is a view of a longitudinal section of a reactor according to the invention, perfused for the culture of fibroblasts of the alveolo-dental ligament, with functional stimulation.

The reactor shown in FIG. 6 comprises an <<alveolated>> vessel 302 which is preferably made of bio-glass, with a trunk-cone alveola which ensures the interface with internal cone 313 (solid part of the implant, for example of the ligaplant) and hence obtaining a mechanical stimulation of the culture with a shearing effect which approaches the physiological conditions to which the periodontal ligament is exposed and with a dilatation-compression effect allowing an homogeneous diffusion of the culture medium between the rigid walls. The size of the device can be adapted to suit the culture desired (trunk-cone), and so the quantity of cells. Preferably, the space between the internal cone 313 and the alveola is 0.2 ±0.1 mm.

Vessel 302 can be inserted into vessel 301, preferably made of a polymer, for example PTFE, which has a cover 303 which is also advantageously made of polymer. Vessel 301 possesses a flat bottom constructed so that the reactor may be used if required on a heating table and so ensure a homogenous temperature distribution. The temperature regulation system can also be directly incorporated in the wall of vessel 301 of the bio-reactor. There too, it can involve circulation of water or even electrical resistance or a Peltier-effect transistor, etc.

Two centered axes 308 are inserted in cover 303 and body 301.

In the mass of the alveola 302 there are for preference entries-exits 309 intended to allow circulation of the medium. These entries-exits, the number of which depends on the length of the solid part (e.g., the radicular part) of implant 313, are distributed in vertical lines, at 90° to one another in a plane and alternating to obtain optimal diffusion of the medium. These entries-exits are most often two or three in number. The arrangement of the vertical slots can also be carried out as for that of an alveola in four quarters. Openings 310 are also made in vessel 302 to allow the passage of the connection tubes and tips or those of the threads allowing a locking mechanism if required. A lower toric joint 312, flexible and thick, controls the amplitude of the vertical movement applied to the medium. The latter is preferably applied at an amplitude of 0.1±0.05 mm for a period of 10 seconds.

The device also comprises, in nut 307, an implant carrier 304 in which can be inserted internal cone 313 and the axis of disinsertion 305 of said cone. A security key 306 provided on the axis of disinsertion 305, allows blocking of the rotation of the mobile assembly carrying the implant and which comprises pieces 305, 306, 307, 304 and 313. A diaphragm 311, associated with the cylinder, prevents the rotation of the mobile assembly.

Such a device allows the optimization and equalization of the flux of nutrient medium due to the multiple entries-exits provided.

The invention can be operated with different types of implants, various forms, structures and compositions and for different applications. Advantageously, it involves a dental implant, the radicular part of which is covered with cells by means of a reactor according to the invention.

I claim:

1. A reactor for cell or tissue culture, comprising (i) a culture chamber defining, between two walls, a culture space of between 1 and 1000 microns, (ii) means of mechanical stimulation of the cells or tissues in said space.

2. The reactor for cell or tissue culture according to claim 1, wherein the culture space is of between 50 and 800 microns.

3. The reactor for cell or tissue culture according to claim 1, comprising (i) a culture chamber defining, between two walls, a culture space of between 1 and 1000 microns, (ii) means of mechanical stimulation of the cells or tissues in said space and (iii) means of perfusion of the culture medium within the culture space.

4. The reactor according to claim 1, wherein the walls defining the culture space are of a biocompatible material.

5. The reactor according to claim 4, wherein the biocompatible material is polymer, glass, plastic, metal, bioglass, bone or coral.

6. The reactor according to claim 4, which involves a culture space defined by two walls in biocompatible material, at least one of which is composed of a material that promotes cell culture.

7. The reactor according to claim 6, wherein one of said two walls is composed of bioglass, bone or coral.

8. The reactor according to claim 1, wherein at least one of the two walls is mobile.

9. The reactor according to claim 1, for the preparation of an implant comprising a core covered wholly or in part by cells.

10. The reactor according to claim 9, wherein one of the walls is formed by the core of the implant itself.

11. The reactor according to claims 1, for the preparation of an implant, characterized in that it includes a culture chamber defined by a rigid wall in biocompatible material, said chamber having a cylindrical or conical form, and means to support the core of the implant, the implant having a form suited to that of the chamber and the means of support being distributed or controlled so that the introduction of the core of the implant forms, between the wall of the chamber and that of the core, a reduced culture space.

12. The reactor according to claim 1, wherein the culture chamber of the reactor is defined by a non-rigid, elastically deformable wall.

13. The reactor according to claim 1, wherein the means of mechanical stimulation of the cells or tissues involve means of displacement of at least one of the walls of the culture space.

14. The reactor according to claim 1, wherein the means of displacement generate in the culture space a force of pressure, stretching, shearing and/or rubbing.

15. The reactor according to claim 1, wherein the means of displacement produce a change in the thickness of the culture space.

16. The reactor according to claim 15, wherein the means of displacement produce a change in the thickness of the culture space less than or equal to about 20% of the initial thickness of the culture space.

17. The reactor according to claim 1, wherein the mechanical stimulation is obtained by means of displacement of the core of the implant by a forwards and backwards movement and/or by a partial rotation in the axis of the core of the implant.

18. The reactor according to claim 1, wherein the mechanical stimulation is obtained by deformation of the culture chamber or a part of it and in that the reactor includes means of deformation of said chamber.

19. A reactor according to claim 18, wherein said deformation is obtained by means of a deformable joint or an elastic wall.

20. The reactor according to claim 1, which includes in addition means of perfusion and diffusion of the culture medium within the culture space.

21. The reactor according to claim 1, which includes in addition means of perfusion and diffusion of the culture medium within the culture space, the diffusion of the medium being obtained by periodic expansion-contraction of the culture space and/or movement cycle at between 1 and 80 cycles per minute, over all the surfaces.

22. The reactor according to claim 1, which includes in addition means of perfusion and diffusion of the culture medium within the culture space and includes one or more entries and exits for the supply and removal of medium the exits and entries being alternated to allow optimal diffusion of the medium.

23. The reactor according to claim 22, wherein the one or more entries and exits are distributed in a plane, with 90° between each.

24. The reactor according to claim 1, which includes in addition means of temperature regulation of the culture medium.

25. The reactor according to claim 24, wherein means of temperature regulation of the culture medium are chosen from circulating water, liquid, at a controlled temperature, gas, electrical resistance and a transistor.

26. The reactor according to claim 1, for the growth, culture, differentiation and/or adhesion of fibroblasts, cementoblasts or chondrocytes, or precursors of these cells.

27. A reactor (2) for the preparation of an implant by cell growth and/or differentiation, comprising an alveola (28) for the culture, differentiation and/or cell growth, wherein said alveola (28) is defined by an elastically deformable membrane (26) and in that the reactor (2) comprises the means of deformation of said membrane (26).

28. The reactor according to claim 27, wherein the means of deformation of said membrane (26) include means (52) of establishing a pressure difference between the two sides of the membrane (26).

29. The reactor according to claim 27, which includes a body (10) defining with the membrane (26) a watertight chamber (42), and in that means (52) of establishing a pressure difference involves a pump connected to said watertight chamber (42).

30. The reactor according to claims 27, which comprises a perfusion system, allowing the supply and renewal of the medium in which the cells are immersed.

31. The reactor according to claim 27, which comprises a perfusion system, allowing the supply and renewal of the medium in which the cells are immersed, the membrane (26) being impermeable and having a passage (36) for perfusion of culture medium.

32. The reactor according to claim 27, wherein the membrane (26) is able to maintain between a core (30) of the implant and the membrane (26) a gap of between 0.1 and 5 mm.

33. The reactor according to claim 27, which includes means for mechanical stimulation of the cells, said means of simulation involving means of displacement of the core of the implant with respect to said alveola (28).

34. A reactor (2) for the preparation of an implant covered in a matrix composed in whole or in part of cells, said reactor comprising:
    a membrane (26) defining an alveola (28) for receiving all or part of the core (30) of the implant and the cells, said membrane (26) being elastically deformable;
    means (58) of support of said implant with its matrix (30) in the alveola (28);
    means of deformation of said membrane (26); and
    a perfusion system allowing supply or renewal of the medium in which the cells are immersed in said alveola.

35. A method for preparing a dental implant, which method comprises (a) immersing a radicular part of an implant covered by cells into a reactor for cell or tissue culture, comprising (i) a culture chamber defining, between two walls, a culture space of between 1 and 1000 microns, (ii) means of mechanical stimulation of the cells or tissues in said space, whereby cells are allowed to grow and/or differentiate on said implant, and (b) extracting the dental implant from the reactor.

36. A reactor (2) for the preparation of a dental implant by cell growth on a radicular part (30) of the implant, including:
    a membrane (26) defining an alveola (28) for receiving the radicular part (30) of the implant;
    means (58) of support of said implant with its radicular part (30) in the alveola (28); and
    means of mechanical stimulation of the cells on the radicular part (30) of the implant;
    wherein said membrane (26) is elastically deformable and means of mechanical stimulation include means of deformation of said membrane (26).

37. A process for the manufacture of an implant by cell growth and/or culture and/or differentiation on a solid adhesion support within the culture medium, said process including:
    bringing the core of the implant into contact with the cells, under conditions that allow the adhesion of cells to said core of the implant or to a part of it;
    the immersion of at least a part of the core of the implant covered in cells obtained above in the alveola or the culture space of a bioreactor according to claim 1, previously or concomitantly filled with culture medium; and
    the mechanical activation of the cells.

38. The process according to claim 37, wherein the solid adhesion support is the core of the implant.

39. A process for the preparation of a dental implant by cell growth on a radicular part (30) of the implant, including:
    the placing of a cell tissue around the radicular part (30) of an implant core (4);
    the immersion of the radicular part (30) covered in cell tissue in an alveola (28) filled with culture medium, the alveola (28) being defined by an elastically deformable membrane (26); and
    the mechanical activation of the membrane (26) to deform it over time.

40. The process according to claim 39, wherein the mechanical activation of the membrane (26) is ensured by establishment of a pressure difference between the two faces of the membrane (26).

41. A reactor for cell or tissue culture, comprising (i) a culture chamber defining, between two walls, a culture space of thickness less than about 1000 microns, (ii) means of mechanical stimulation of the cells or tissues in said space and (iii), means of perfusion of the culture medium within the culture space, the culture space comprising in addition elements that allow the mechanical stimulation to be increased or having at least one wall exhibiting irregularities.

42. The reactor according to claim 41, wherein elements that allow mechanical stimulation to be increased are chosen from sponge, fiber, bead and particle.

43. The reactor according to claim 41, wherein elements having at least one wall exhibiting irregularities are chosen form grooves and spay.

* * * * *